United States Patent [19]

Nho

[11] Patent Number: 5,478,806
[45] Date of Patent: Dec. 26, 1995

[54] ENHANCEMENT OF ANTITUMOR THERAPY WITH HEMOGLOBIN-BASED CONJUGATES

[75] Inventor: Kwang Nho, Somerset, N.J.

[73] Assignee: Enzon, Inc., Piscataway, N.J.

[21] Appl. No.: 213,881

[22] Filed: Mar. 16, 1994

Related U.S. Application Data

[63] Continuation-in-part of Ser. No. 960,007, Oct. 13, 1992, Pat. No. 5,312,808, and a continuation-in-part of Ser. No. 888,039, May 22, 1992, Pat. No. 5,386,014, which is a continuation of Ser. No. 440,553, Nov. 22, 1989, abandoned.

[51] Int. Cl.$^6$ .................. C70K 14/805; A61K 38/42
[52] U.S. Cl. ...................... 514/6; 530/385; 604/20
[58] Field of Search .................. 514/6; 530/385; 604/20

[56] References Cited

U.S. PATENT DOCUMENTS

| | | | |
|---|---|---|---|
| 3,966,902 | 6/1976 | Chromecek | 424/59 |
| 4,179,337 | 12/1979 | Davis et al. | 435/181 |
| 4,861,876 | 8/1989 | Kessel | 540/145 |
| 5,122,614 | 6/1992 | Zalipsky | 548/520 |
| 5,173,426 | 12/1992 | Fischer et al. | 435/252.3 |
| 5,234,903 | 8/1993 | Nho et al. | 514/6 |
| 5,239,061 | 8/1993 | Fronticelli et al. | 530/385 |
| 5,264,555 | 11/1993 | Shorr et al. | 530/385 |
| 5,295,944 | 3/1994 | Teicher et al. | 600/1 |
| 5,296,465 | 3/1994 | Rausch et al. | 514/6 |
| 5,296,466 | 3/1994 | Kilbourn et al. | 514/6 |
| 5,312,808 | 5/1994 | Shorr et al. | 514/6 |

OTHER PUBLICATIONS

Teicher et al., Art. Cells, Blood Subs., and Immob. Biotech. 22(3) 827–833 (1994).
Teicher et al., Biomat., Art. Cells & Immob. Biotech. 20(2–4), 657–660 (1992).
Teicher, Biomat., Art. Cells & Immob. Biotech., 20(2–4), Var. 875–910 (1992).
Teicher et al, Biomat., Art. Cells & Immob. Biotech., 20(2–4), 657–660 (1992).
Nho et al, "Increased Oxy. Ten. in Sol. Tum. following PEG–Hb trans.", Blood Substitutes & Related Prod., IBC, Philadelphia, (Sep. 21–22, 1993).
Hirst et al Br. J. Cancer, 55, 487–491 (1987).
Siemen et al, Int. J. Radiation Oncol. Biol. Phys., 16, 1169–1172 (1989)
Teicher et al, J. Cancer Res. Clin. Oncol., 118, 123–128 (1992).
Wu et al, Cancer Res., 53, 3765–3770 (Aug. 15, 1993).
Winslow, "Hemoglobin Based Blood Substitutes", Blood Substitutes & Related Products, IBC, Philadelphia (Sep. 21–22, 1993).
Coleman, ASTRO Refresher Course #409 "Hypoxic Cell Sensitizers" (Oct. 18, 1990).
Teicher et al, Biomat., Art. Cells, Art. Org., 16(1–3) 533–546 (1988).
Rockwell, Biomat., Art. Cells, Art. Org., 16(1–3), 519–531 (1988).

Primary Examiner—Jill Warden
Assistant Examiner—Carol A. Salata
Attorney, Agent, or Firm—Steinberg, Raskin & Davidson

[57] ABSTRACT

The use of hemoglobin-polymer conjugates to enhance antitumor therapy in mammals is disclosed. The methods include administering an effective amount of an antitumor therapy such as radiation in combination with hemoglobin conjugated to a substantially non-antigenic polymer.

29 Claims, 4 Drawing Sheets

ENHANCEMENT OF ANTITUMOR THERAPY WITH HEMOGLOBIN-BASED CONJUGATES

CROSS-REFERENCES TO RELATED APPLICATIONS

This application is a Continuation-In-Part of U.S. patent application Ser. No. 07/888,039, now U.S. Pat. No. 5,386,014 filed May 22, 1992, which is a continuation of U.S. patent application Ser. No. 07/440,553, now abandoned. This application is also a Continuation-In-Part of U.S. patent application Ser. No. 07/960,007, filed Oct. 13, 1992, now U.S. Pat. No. 5,312,808. The disclosure of each of these applications is incorporated herein by reference.

BACKGROUND OF THE INVENTION

1. Field of the Invention

The present invention relates to enhancing antitumor therapies with hemoglobin-polymer conjugates.

2. Description of Related Art

Solid tumor masses are often hypoxic in mammals. This local hypoxia is believed to be at least somewhat responsible for reducing the effectiveness of current antitumor treatments. In the past, some have investigated whether increasing oxygen inspiration during chemotherapy or radiation could improve tumor kill. While such tactics have intuitive appeal, it is believed that none have investigated whether increasing oxygen levels directly at the site of the lesion would improve antitumor therapy. The present invention addresses this issue and is described below.

SUMMARY OF THE INVENTION

The present invention provides methods of enhancing the effectiveness of antitumor treatments such as radiation and/or chemotherapeutic agent therapies. Methods of reducing tumor burden in mammals are also provided. The methods include administering to a mammal in need of such therapy or therapies an effective amount of hemoglobin conjugated to a substantially non-antigenic polymer in combination with an antitumor therapy. A significant reduction in the tumorous condition results.

The polymer conjugates are preferably in the form of poly(alkylene oxide)-hemoglobin (PAO-Hb) and most preferably poly(ethylene glycol)-hemoglobin (PEG-Hb). The conjugates are administered as part of pharmaceutically-acceptable fluids or solutions as such terms are understood in the art. The solutions contain from about 0.2 to about 40 wt. % conjugates; preferably about 2–20 wt % and most preferably about 10–14 wt % PAO-Hb conjugates. In each case, the conjugates are composed of about 50% Hb.

Suitable hemoglobins for the conjugates include both recombinant, including wild type or mutants, and non-recombinant types which correspond to mammalian species. Human and ruminant hemoglobins such as bovine hemoglobins are preferred.

The amount of PAO-Hb conjugate administered is dependent on several factors including tumor type, tumor burden, the amount of radiation and whether chemotherapeutic agents will also be administered. While the preference of the artisan will ultimately prevail, the amount of PAO-Hb administered will range from 0.24–6.30 g/kg.

The Hb-conjugates are preferably administered in combination with a form of radiation therapy. Chemotherapy can also be included. The combination of therapies principally includes administering the hemoglobin conjugates prior to, or at the same time as the other antitumor therapies.

The present invention has several advantages over the prior art. It has unexpectedly been found that the Hb-polymer conjugates preferentially localize in hypoxic areas including tumor lesions. Thus, the hemoglobin conjugates synergistically enhance radiation and/or chemotherapy by providing high levels of oxygen locally.

For a better understanding of the present invention, reference is made to the following detailed description, and its scope will be pointed out in the appended claims.

DETAILED DESCRIPTION OF THE INVENTION

A. Introduction

Figure 1:
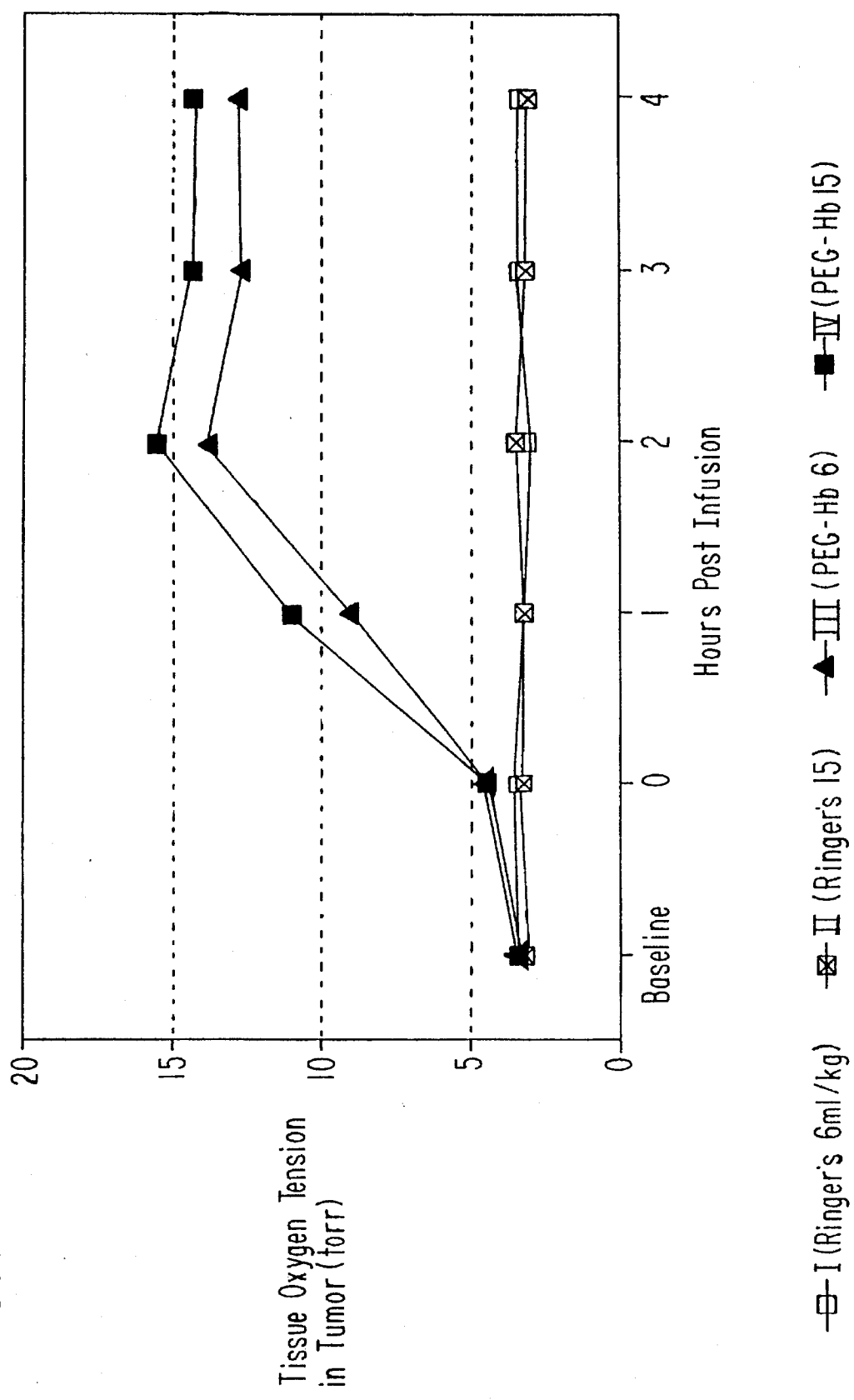
FIG. 1 illustrates a comparison of average tissue oxygenation in rat osteogenic sarcoma after administration of 6 or 15 ml/kg of either PEG-Hb or Ringer's Lactate.

The above-identified related applications as well as U.S. Pat. No. 5,234,903, the contents of which are hereby incorporated by reference, disclose various aspects relating to poly(alkylene oxide)-conjugated hemoglobins. In addition to the utility of PAO-Hb conjugates as a treatment for hypovolemia, shock and anemia, additional research with the conjugates has now revealed that these compositions unexpectedly enhance the effectiveness of antitumor treatments.

B. Treatment

The terms "treat" and "treatment" as used herein refer to medical intervention. The terms relate to repair, reduction, prevention or alleviation of tumorous conditions in mammals. For purposes of the present invention, "tumorous condition" and "tumor" are understood to include their generally accepted medical meanings. Thus, the terms describe physiologic conditions in mammals relating to, or caused by, a neoplastic growth such as that associated abnormal or malignant cellular proliferation.

C. Antitumor Therapy

The invention includes a method of enhancing the effectiveness of antitumor therapy in mammals. In this aspect, a mammal in need of such therapy is administered an effective amount of an antitumor therapy in combination with hemoglobin conjugated to a substantially non-antigenic polymer.

For purposes of the present invention, antitumor therapy is understood to mean a therapy specifically designed to combat neoplastic growth. The therapy preferably connotes radiation although chemotherapy and combinations thereof are also within the scope.

The term "radiation" is used in a manner consistent with its customary medical meaning. Most commonly, X-ray or gamma radiation is administered using standard radiation-emitting apparatus. The radiation is directed specifically at the site of the tumor, although regional or even complete body doses can be administered to reduce tumor size. Tumor cell death is believed to result from the effects of ionization of $O_2$ into $O_2^-$ and/or $OH^-$. The conjugates, which preferentially localize in hypoxic areas, thus act synergistically with any radiation therapy which relies, at least in part, on the presence of oxygen for an effect.

The dose of radiation administered can broadly range from 1 to 70 Grays (1 Gy=100 rads). The exact amount given is dependant upon several factors including tumor size and location, patient age, physical condition and other conditions known to those of ordinary skill in the art. When included as part of the inventive method, the radiation is preferably given in amounts ranging from 10–50 Gy in the form of a single or fractionated doses.

The method can also include the administration of chemotherapeutic agents in addition to or in place of radiation. Within this aspect is the administration of agents known for their specific activity against neoplastic conditions. A non-limiting list of suitable agents include:

a. alkylating agents such as cyclophosphamide, cis-platin, carboplatin;

b. alkaloids such as vincristine, vinblastine, taxoids and the like; and c. doxorubicin, methotrexate, bleomycin, misonidazole and others.

It is understood that these agents are given within their known dosage ranges when used to treat tumors.

D. Hemoglobin Conjugates

In a preferred embodiment, the conjugates include poly(alkylene oxide) modified hemoglobins such as those disclosed in the parent patent applications already incorporated by reference herein. In particular, the poly(alkylene oxide) hemoglobin (PAO-Hb) conjugates are preferably administered in physiologically-acceptable solutions.

The conjugate is preferably formed by covalently bonding the hydroxyl terminals of the poly(alkylene oxide) and the free amino groups of lysine residues of the hemoglobin. See U.S. Pat. No. 5,234,903, which discloses PEG succinimidyl carbonate-Hb. Other art-recognized methods of conjugating the polymers with the Hb proteins, such as by via an amide or ester linkage, are also suitable for use with the present invention. While epsilon amino group modifications of hemoglobin lysines are preferred, other conjugation methods are also contemplated. Covalent linkage by any atom between the hemoglobin and polymer is possible. Moreover, non-covalent conjugation such as lipophilic or hydrophilic interactions are also contemplated. Moreover, polyethylene glycol-based liposomes containing either Hb alone or as a PAO-Hb conjugate are also contemplated.

Although the preferred conjugates used herein include poly(alkylene oxides), alternative non-antigenic polymeric substances are also useful. Within this class are materials such as dextran, polyvinyl pyrrolidones, polysaccharides, starches, polyvinyl alcohols, polyacryl amides or other similar substantially non-immunogenic polymers. Those of ordinary skill in the art will realize that the foregoing is merely illustrative and not intended to restrict the type of non-antigenic polymer suitable for use herein.

The conjugate substituents are typically reacted under conditions which are appropriate to effect conjugation of the polymer and hemoglobin yet retain the ability of the hemoglobin or hemoglobin-like substance to transfer oxygen. The reactants are combined so that there is a several-fold molar excess of the polymeric substance over the hemoglobin. The reactions are carried out at temperatures of from about 0° to about 25° C. over time periods ranging from a few minutes to as long as 12 hours. Following the conjugation reaction, the desired product is recovered using known techniques and purified using column chromatography or similar apparatus if necessary.

By controlling the molar excess of the polymer reacted with the hemoglobin, the artisan can tailor the number of polymeric strands attached. Preferable conjugates contain around 11 strands of PEG have been made by reacting about a 15 to 20 fold molar excess of an activated PEG with hemoglobin.

The hemoglobin conjugates preferably have a molecular weight of at least about 85,000 daltons and a degree of substitution of at least 5 poly(alkylene oxide) conjugates per hemoglobin molecule. More preferably, the conjugates have a molecular weight of at least 100,000 daltons and at least 8 poly(alkylene oxide) strands per hemoglobin conjugate. Most preferred conjugates have a molecular weight of at least 120,000 daltons and at least 11 poly(alkylene oxides) per hemoglobin molecule.

E. Polymer Portion of Conjugate

The conjugates preferably include polyethylene glycol (PEG) as the poly(alkylene oxide). The poly(alkylene oxides) include monomethoxy-polyethylene glycol, polypropylene glycol, block copolymers of polyethylene glycol and polypropylene glycol and the like. The polymers can also be distally capped with $C_{1-4}$ alkyls instead of monomethoxy groups.

To be suitable for use herein, the poly(alkylene oxides) must be soluble in water at room temperature. Poly(alkylene oxides) having a molecular weight from about 200 to about 20,000 daltons are preferable for use herein, with PAO's having molecular weights of from about 2,000 to about 10,000 being preferred and PAO's having a molecular weight of about 5,000 being particularly preferred.

F. Hemoglobin Portion

The hemoglobin (Hb) portion of the conjugates can be obtained from any appropriate mammalian source, human or non-human. Human hemoglobin can be obtained from whole human blood which has either been freshly drawn or obtained from "out-dated" supplies from blood banks. Human hemoglobin can also be obtained from placentas or packed erythrocytes obtained from blood donor centers. The hemoglobin can also be obtained from recombinant methods including the establishment of transgenic herds or cells. Such transgenic animals express wild type human, variant human, or mutated human hemoglobins, for example. Non-human hemoglobins include ruminant hemoglobins, such as bovine and/or ovine sources. Porcine hemoglobins are also of use. Mammalian-species specific hemoglobins are also contemplated. Pharmaceutically-acceptable solutions containing mixtures of various types of Hb conjugated to the poly(alkylene oxides) are also contemplated. The hemoglobin portion can account for about 20–80 percent of the weight of the conjugates.

G. Hemoglobin-Conjugate Solutions

The amount of conjugates contained in the solution can be in a range of about 0.2–40 wt %; solutions containing about 2–20 are preferred and solutions containing about 10–14 wt% are most preferred. Such solutions are capable of delivering conjugates having an in vivo half life of at least 2 hours, preferably, at least 6–18 hours and most preferably at least 12–20 hours in mammals. Preparations having in vivo half lives of about 40–60 hours in mammals are also contemplated. It is to be understood that the actual half life of the conjugates in vivo will depend upon several factors including the species, sex and weight of the mammal and dosage administered.

H. Amount of Conjugate Administered

The amount of the conjugate administered is an amount which significantly enhances antitumor therapy. Evidence of enhancement can be deduced by observation or by analytical measurements of increased local muscle/tissue/organ oxygen levels using apparatus designed for such purpose. One such apparatus is an OxySpot/OxyMap available from Medical Systems of Greenvale, N.Y. The maximum dose is the highest dosage that does not cause clinically important side effects. For purposes of the present invention, such side effects in humans include clinically important hypervolemia, iron overload, renal damage, etc. The conjugates are usually administered directly into the bloodstream such via intravenous infusion or transfusion. In the case of transfusional therapy, the solutions can be administered in amounts ranging up to 70% of the patient's blood volume. It will be understood that the fluids may also contain pharmaceutical necessities such as buffers, preservatives, etc. as such ingredients are utilized in the art.

The amount of the conjugate will depend upon several factors. For example, the tumor size, type of tumor, type of radiation and/or chemotherapy as well as the concentration of the conjugated hemoglobins included in the administered solution all will effect the amount administered. As a general guideline, PAO-Hb conjugates are administered in amounts ranging from 0.24–6.3 g/kg and preferably in amounts ranging from 0.72–2.0 g/kg.

I. Combination Therapy

As used herein, the term "in combination with" is understood to mean that the Hb-conjugates are administered to the mammal within a time period that allows the conjugates to synergistically interact with the radiation and/or chemotherapeutic agent. In situations where the conjugates are administered in combination with radiation therapy, the conjugates are preferably given at least about 2–4 hours before each radiation dose. In the case of chemotherapeutic agents, the conjugates are administered as part of an ongoing polypharmaceutical regimen.

EXAMPLES

The following examples serve to provide further appreciation of the invention but are not meant in any way to restrict the effective scope of the invention.

EXAMPLE I

In this Example, the ability of PEG-Hb conjugates to preferentially localize in osteogenic sarcoma tumor areas was demonstrated using PEG-Hb prepared according as described in U.S. Pat. No. 5,234,903 using bovine Hb and contained 12 g % conjugates (approx. 50% Hb), methemoglobin <5%. The OxyMap™ apparatus, a product of Medical Systems, Greenvale, NY, was used to measure oxygen tension in osteosarcoma in rats. The oxygen measurement protocols of Rumsey, W. R. et al in Science 241:1649–51 (1988) and Wilson et al in Cancer Res. 52:3988–93 (1992) were followed.

Twelve Sprague-Dawley rats (approx. 200–250 g, female) were each injected subcutaneously with approximately $1 \times 10^7$ osteosarcoma cells (0.1 ml). The UMR106 tumor cell line was obtained from ATCC. After the tumors had grown to about 1.5 cm³ in diameter, the rats were anesthetized with 20 mg/kg sodium pentobarbital to make a skin incision to expose the tumor. The rats were divided into four groups of three. Two groups received a single bolus IV injection of PEG-Hb while the other groups received single bolus IV injections of Ringer's Lactate. The dosing of the rats in each group was as follows:

Group I: Ringer's Lactate @6 ml/kg
Group II: Ringer's Lactate @15 ml/kg
Group III: PEG-Hb @6 ml/kg
Group IV: PEG-Hb @15 ml/kg.

The average baseline tissue oxygen tension in the tumors (n=12) was determined to be about 3.5–4 torr.

RESULTS

A. Group I v. Group III

Referring now to FIG. 1, the effect of a 6 ml/kg bolus injection of PEG-Hb compared to Ringer's lactate is shown. With PEG-Hb, tissue oxygen tension rose immediately from the baseline 3.5–4 torr. to 4.5 torr. After one hour, tissue oxygen tension rose to about 9 torr. Two hours after the bolus injection, tissue oxygen tension rose to about 13 torr and remained at about this level for at least 2 more hours before the study was ceased. The Ringer's lactate injection failed to provide any noticeable improvement in local oxygenation.

B. Group II v. Group IV

Similar to the results described above, the effect of a bolus injection of 15 ml/kg PEG-Hb compared to Ringer's lactate 15 ml/kg is seen. With PEG-Hb, tissue oxygen tension rose to 15.6 torr two hours after injection and remained at about this level for at least two more hours. The Ringer's lactate injection again failed to raise tumor oxygenation.

EXAMPLE II

In this example, the synergy of PEG-Hb with radiation therapy was demonstrated in rats. The gamma ray apparatus was a Gamma 40 (Atomic Energy, Inc.). The PEG-Hb solution was the same as that described in Example 1.

Forty Sprague-Dawley rats (weighing approx. 200–250 g,) were injected with a 0.1 ml solution containing approximately $1 \times 10^7$ osteogenic sarcoma cells (UMR106, ATCC) in the right hindquarter. The tumors were allowed to grow to about 1.5 cm³ in volume. The rats were divided into four equal groups of ten.

The first group (A) received 15 ml/kg Ringer's lactate without any radiation. The second group (B) received 15 ml/kg of Ringer's lactate and a single 4 Gy gamma radiation dose. The third group (C) received 6 ml/kg PEG-Hb and a single 4 Gy gamma radiation dose. The final group received 15 ml/kg PEG-Hb and a single 4 Gy gamma radiation dose. All solutions were administered via the tail vein. The radiation was administered two hours later.

On the day of the experiments, the animals were anesthetized using 20 mg/kg of sodium pentobarbital by i.p. injection. The animals were placed on heating pads and their body temperature is maintained at 38–39 degrees.

Figure 2:
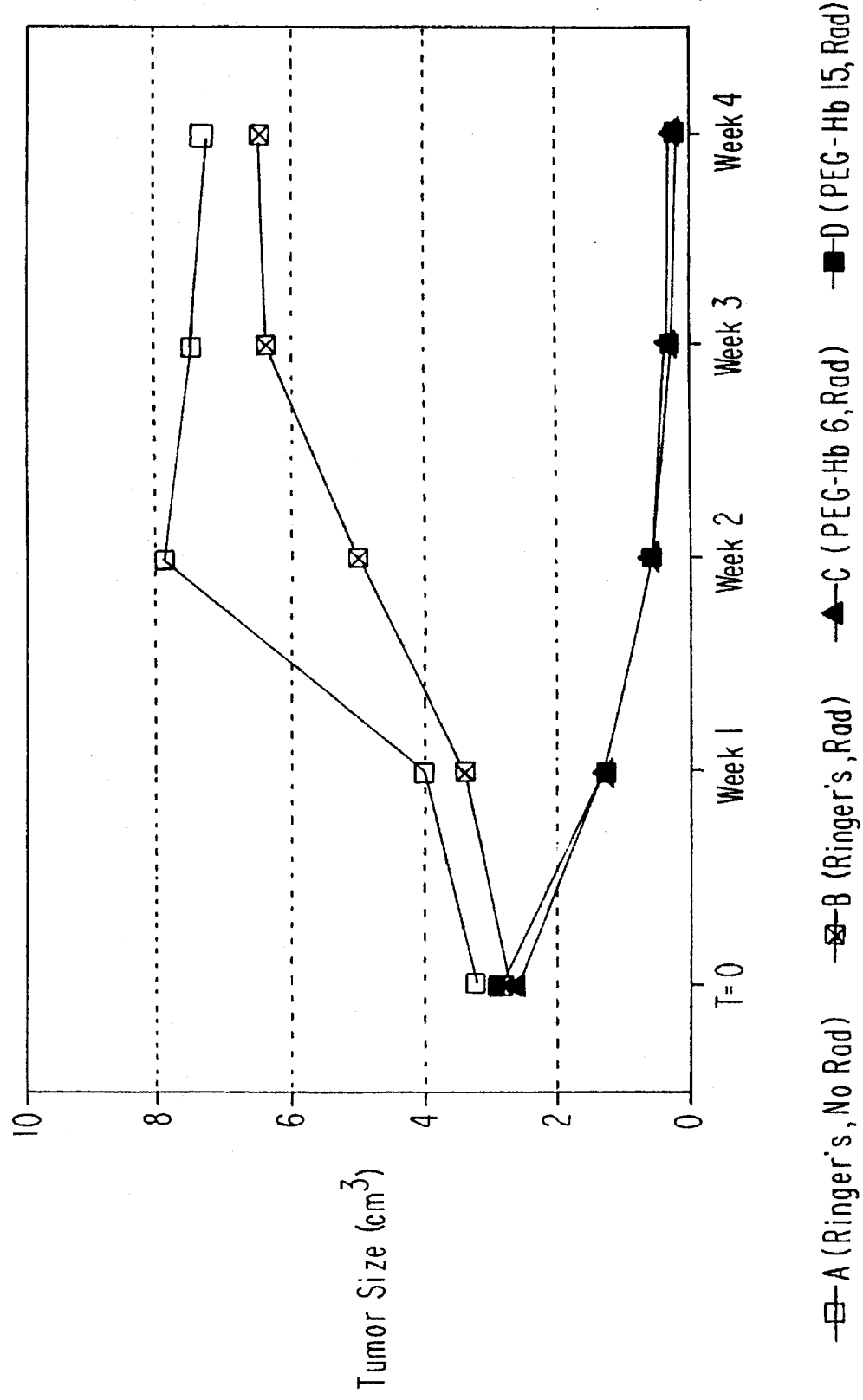
FIG. 2 illustrates a comparison of rat osteogenic sarcoma tumor sizes after various treatments.
Figure 3:
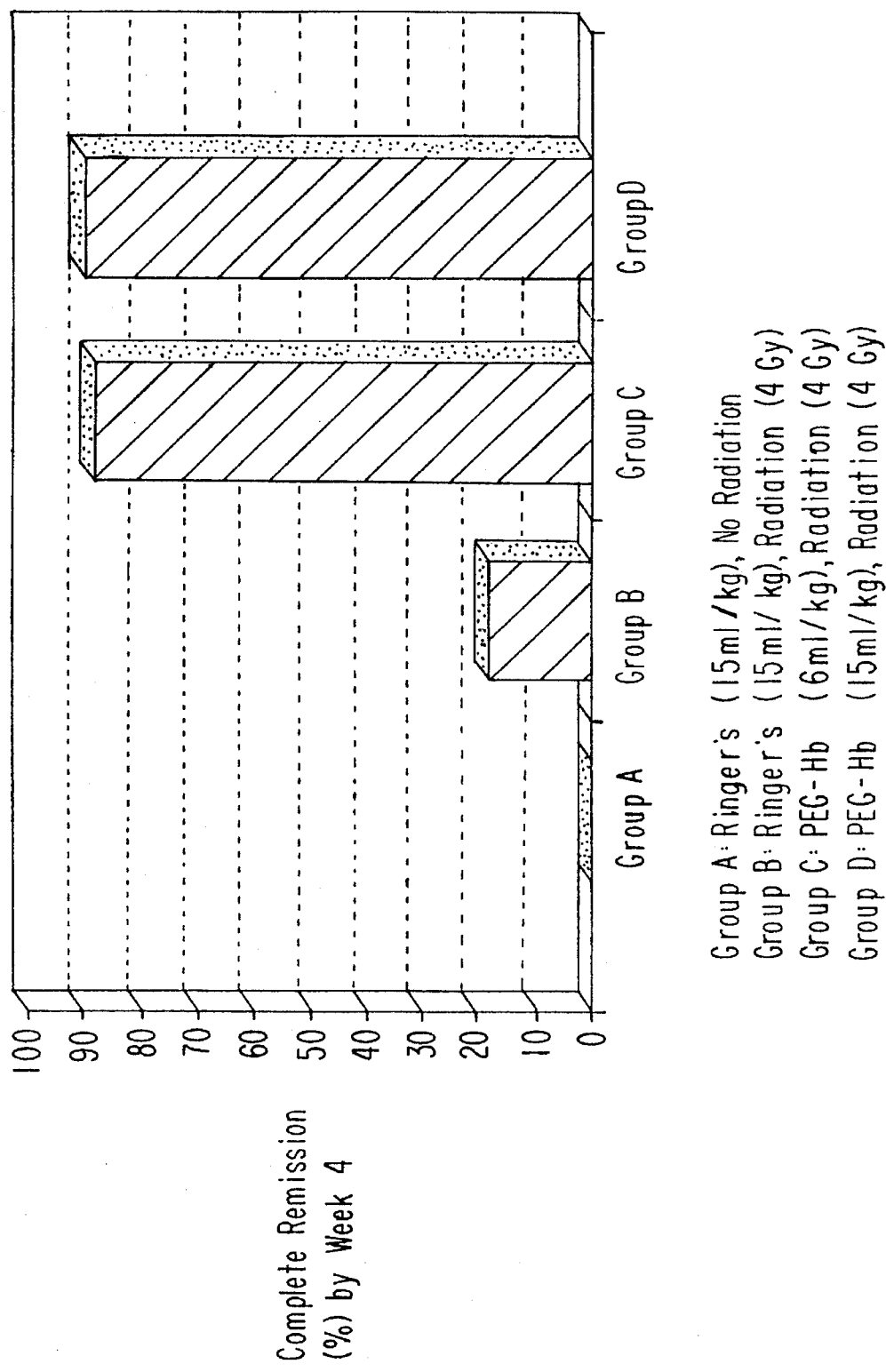
FIG. 3 illustrates the ability of various treatments to achieve complete remission of rat osteogenic sarcoma.

The osteosarcoma was measured prior to the radiation, after one, two, three, and finally, after four weeks. The average results are set forth in FIG. 2. Osteosarcomas larger than 1.5 cm³ are hypoxic, with surface tissue oxygen tensions of from 0–5 torr, as determined with the OxySpot/OxyMap apparatus, (described above). The value of adding PEG-Hb is dramatically shown in FIG. 2. In both groups C and D virtually no sarcoma was found four weeks after the administration of the conjugates in combination with the radiation. The Ringer's control groups showed continued tumor growth. FIG. 3 shows the rates of complete remission in the rats given the various treatment methods described herein. Tumor size was measured externally with calipers. The dramatic synergy achieved by including PEG-Hb with radiation is shown for groups C and D.

EXAMPLE III

In this Example, the ability of PEG-Hb conjugates to preferentially localize in tumor areas was demonstrated using the same type of PEG-Hb conjugates described above in Example I. The OxyMap™ apparatus, a product of Medical Systems, Greenvale, N.Y., was used to measure oxygen tension in C6 glioma in rats. The oxygen measurement protocols of Rumsey, W. R. et al in Science 241:1649–51 (1988) and Wilson et al in Cancer Res. 52:3988–93 (1992) were followed.

Twelve Wistar rats (150–200 g, female) obtained from Charles River Laboratories of NJ were each injected subcutaneously with approximately $2 \times 10^6$ C6 glioma cells. Tumor cell line was obtained from ATCC. After the tumors had grown to about 1–2 cm in diameter, the rats were anesthetized with 20 mg/kg sodium pentobarbital to make a skin incision to expose the tumor. The rats were divided into four groups of three. Two groups received PEG-Hb while the other groups received Ringer's Lactate. The dosing of the rats in each group was as follows:

Group I: Ringer's Lactate @6 ml/kg
Group II: Ringer's Lactate @15 ml/kg
Group III: PEG-Hb @6 ml/kg
Group IV: PEG-Hb @15 ml/kg.

The average baseline tissue oxygen tension in the tumors (n=12) was determined to be 3.5–4 torr.

RESULTS

A. Group I v. Group III

Figure 4:
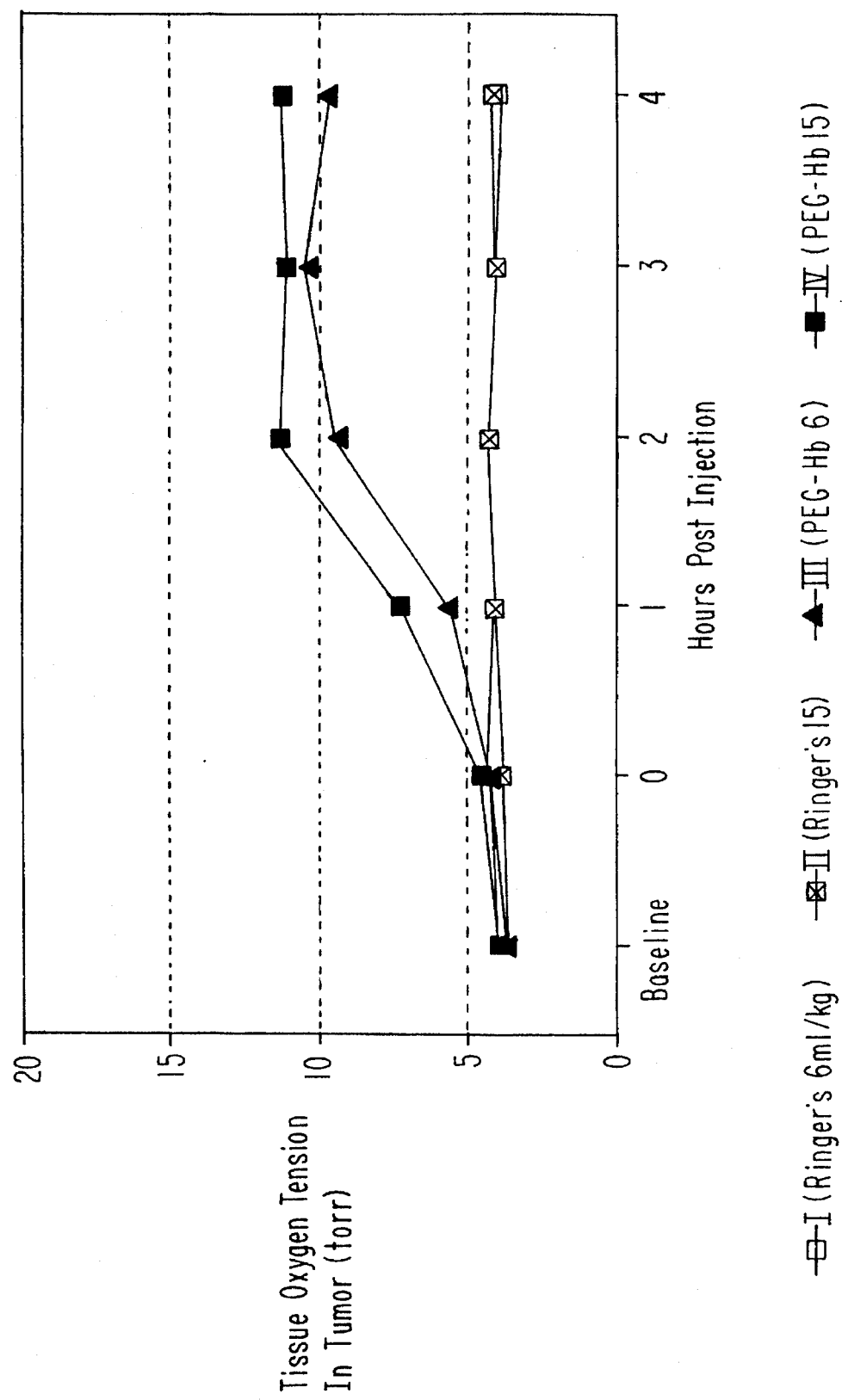
FIG. 4 illustrates a comparison of average tissue oxygenation in rat C6 glioma after administration of 6 or 15 ml/kg of either PEG-Hb or Ringer's Lactate.

Referring now to FIG. 4, the difference between a bolus injection of 6 ml/kg PEG-Hb and Ringer's lactate is shown. With PEG-Hb, tissue oxygen tension rose from the baseline 3.5–4 torr. to 5.5 torr. after one hour and thereafter to almost 10 torr. The tissue oxygen tension remained high for over 2 hours. The Ringer's lactate injection failed to provide any noticeable improvement in local oxygenation.

B. Group II v. Group IV

In this comparison, the effect of a bolus injection of 15 ml/kg PEG-Hb vs. Ringer's lactate is shown. With PEG-Hb, tissue oxygen tension rose to 11.5 torr two hours after injection and remained at about that level for at least two more hours. The Ringer's lactate injection again failed to raise tumor oxygenation.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A method of enhancing the effectiveness of antitumor therapy in mammals, comprising:
   administering to a mammal in need of such therapy an effective amount of radiation in combination with hemoglobin covalently conjugated to a poly(alkylene oxide), said hemoglobin conjugate being present in an amount sufficient to enhance the effectiveness of said radiation.

2. The method of claim 1, wherein said hemoglobin is selected from the group consisting of recombinant and non-recombinant hemoglobins.

3. The method of claim 2, wherein said hemoglobin is mammalian.

4. The method of claim 3, wherein said mammalian hemoglobin is selected from the group consisting of human and ruminant hemoglobins.

5. The method of claim 4, wherein said ruminant hemoglobin comprises bovine hemoglobin.

6. The method of claim 4, wherein said effective amount of radiation is from about 100–5,000 rads.

7. The method of claim 1, wherein said hemoglobin conjugate is in a pharmaceutically-acceptable fluid.

8. The method of claim 7, wherein the concentration of said hemoglobin conjugate in said fluid is from about 0.02 to about 40 weight percent.

9. The method of claim 8, wherein the concentration of said hemoglobin conjugate in said fluid is from about 2 to about 20 weight percent.

10. The method of claim 8, wherein the concentration of said hemoglobin conjugate in said fluid is from about 10 to about 14 weight percent.

11. The method of claim 1, wherein said poly(alkylene oxide) comprises a polyethylene glycol.

12. The method of claim 11, wherein said poly(alkylene oxide) is selected from the group consisting of monomethoxy(polyethylene glycol), poly(propylene glycol) and block copolymers thereof.

13. The method of claim 1, wherein said hemoglobin conjugate has a molecular weight of at least 85,000 daltons and at least 5 poly(alkylene oxide) conjugates per hemoglobin molecule.

14. The method of claim 13, wherein said hemoglobin conjugate has a molecular weight of at least 100,000 daltons and at least 8 poly(alkylene oxide) conjugates per hemoglobin molecule.

15. The method of claim 14, wherein said hemoglobin conjugate has a molecular weight of at least 120,000 daltons and at least 11 poly(alkylene oxide) conjugates per hemoglobin molecule.

16. The method of claim 1, wherein said poly(alkylene oxide) has a molecular weight of about 1,000 to about 30,000.

17. The method of claim 16, wherein said poly(alkylene oxide) has a molecular weight of about 2,000 to about 25,000.

18. The method of claim 17, wherein said poly(alkylene oxide) has a molecular weight of about 5,000 daltons.

19. The method of claim 1, wherein said hemoglobin conjugate has a circulating half-life of at least 2 hours.

20. The method of claim 19, wherein said hemoglobin conjugate has a circulating half-life of at least 10 hours.

21. The method of claim 20, wherein said hemoglobin conjugate has a circulating half-life of at least 12 hours.

22. The method of claim 1, further comprising administering a chemotherapeutic agent with said combination.

23. The method of claim 1, wherein said hemoglobin conjugate is administered about 2–4 hours before said effective amount of radiation.

24. A method of reducing tumor burden in mammals, comprising administering to a mammal in need of such therapy an effective amount of:

(a) radiation, optionally in combination with a chemotherapeutic agent in combination with (b) hemoglobin covalently conjugated to a polyalkylene oxide, said hemoglobin conjugate being present in amounts sufficient to enhance the effectiveness of said radiation.

25. The method of claim 24, wherein said hemoglobin is selected from the group consisting of recombinant and non-recombinant hemoglobins.

26. The method of claim 24, wherein said hemoglobin is mammalian.

27. The method of claim 26, wherein said mammalian hemoglobin is selected from the group consisting of human and ruminant hemoglobins.

28. The method of claim 27, wherein said ruminant hemoglobin comprises bovine hemoglobin.

29. The method of claim 24, wherein said hemoglobin conjugate is administered about 2–4 hours before said effective amount of radiation.

* * * * *